United States Patent [19]

Haffer et al.

[11] 3,960,842

[45] June 1, 1976

[54] PROCESS FOR THE PREPARATION OF 17β-OXALYL STEROIDS

[75] Inventors: Gregor Haffer; Ulrich Eder; Henry Laurent; Jürgen Ruppert; Gerhard Sauer; Rudolf Wiechert, all of Berlin, Germany

[73] Assignee: Schering Aktiengesellschaft, Berlin & Bergkamen, Germany

[22] Filed: July 12, 1974

[21] Appl. No.: 487,987

[30] Foreign Application Priority Data

July 14, 1973 Germany............................ 2336438

[52] U.S. Cl..................... 260/239.55 C; 260/397.1; 260/999
[51] Int. Cl.².............................................. C07J 7/00
[58] Field of Search................ 260/397.1, 239.55 C; /Machine Searched Steroids

[56] References Cited
UNITED STATES PATENTS 3,824,260  7/1974  Laurent et al. .................. 260/397.1
3,833,563  9/1974  Laurent et al. .............. 260/397.1 X
3,875,194  4/1975  Laurent et al. .................. 260/397.1

OTHER PUBLICATIONS

Bertin et al., Bull. Soc. Chim. France, pp. 1555–1560 (1962).
Lewbart et al., Journ. Org. Chem., pp. 2559–2566 (1964).
Lewbart et al., Journ. Org. Chem. pp. 1779–1786 (1963).

Primary Examiner—Ethel G. Love
Attorney, Agent, or Firm—Millen, Raptes & White

[57] ABSTRACT

20-Cyano-17α-H steroids having as the 17-position substituent the group

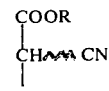

wherein R is H, alkyl of 1–8 carbon atoms or benzyl, having a 13-methyl or 13-ethyl group and which are unsubstituted or substituted with an α-methyl group in the 16-position are converted to the corresponding 20-keto steroids by reaction in an aprotic solvent with a deprotonating agent containing an alkali metal, an alkaline earth metal, copper(I) or thallium(I), and optionally additionally with a copper(I) salt or a thallium(I) salt or a silver(I) salt, and thereafter conducting an oxidative splitting reaction with oxygen. The thus-produced 17β-oxalyl steroids possess pharmacological activity, e.g., anti-inflammatory activity, or are useful as intermediates for the production of pharmacologically active steroids.

17 Claims, No Drawings

PROCESS FOR THE PREPARATION OF 17β-OXALYL STEROIDS

BACKGROUND OF THE INVENTION

This invention relates to a process for the preparation of 17β-oxalyl steroids. It is known that numerous 17β-oxalyl steroids of the general Formula I are pharmacologically effective compounds (Belgian Pat. No. 779,869). The process of this invention makes it possible to produce these compounds in a three-stage synthesis with a simple mode of operation from 17-oxo steroids, because the starting 20-cyano steroids of the process can be conventionally synthesized in a two-step synthesis from the corresponding 17-oxo steroids (J. Chem. Soc., [London],1952, 161; J. Org. Chem. 30, 165, 2715; and U.S. Pat. No. 3,079,385).

SUMMARY OF THE INVENTION

According to the process of this invention, 17β-oxalyl steroids of the general Formula I

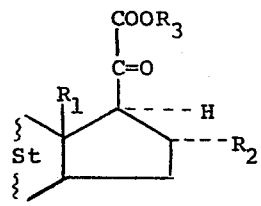

wherein $R_1$ is methyl or ethyl, $R_2$ is a hydrogen atom or methyl, and $R_3$ is a hydrogen atom, alkyl of 1–8 carbon atoms, or benzyl, and St is the remainder of the steroid molecule, are produced by reacting a 20-cyano steroid of the general Formula II

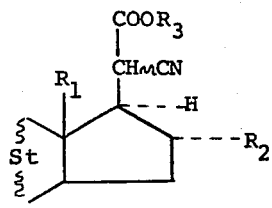

wherein the cyano group is in the α- or β-position, and $R_1$, $R_2$, $R_3$, and St have the values given for Formula I, in an aprotic solvent with a deprotonating agent containing an alkali metal, an alkaline earth metal, copper(I) or thallium(I), and optionally additionally with a copper(I) salt, or a thallium(I) salt or a silver(I) salt, and thereafter conducting an oxidative splitting reaction with oxygen.

The starting compounds for the process of this invention of Formula II have a steroid nucleus which can be saturated or unsaturated, substituted or unsubstituted in the A, B and C rings.

Examples of possible substituents for St are halogen atoms, preferably fluorine or chlorine, e.g., at one or both of the 6 and 9 positions; alkyl, preferably methyl, e.g., at the 2, 4, 6, 7, 8, 9 or 11 position; free, esterified, (preferably alkanoyloxy of 1–8 carbon atoms in the alkanoyl group, and benzoyloxy), or etherified (especially alkoxy of 1–6 carbon atoms in the alkyl group, and benzyloxy) hydroxy groups, e.g., in the 3, 6, 11 or 12 positions; free or ketalized (particularly alkylidenedioxy of 2–6 carbon atoms in the alkylidene group and o-phenylenedioxy) oxo groups, e.g., in the 3, 6, 11 or 12 position; methylene, e.g., in the 11 position; and oxido, e.g., in the 5(6)-position.

Examples of unsaturated steroid residues are those having one double bond, e.g., a $\Delta^3$-, $\Delta^4$-, or $\Delta^5$-double bond, two double bonds, e.g., $\Delta^{1,4}$-, $\Delta^{4,6}$-, $\Delta^{2,5(10)}$-, $\Delta^{3,5}$-, $\Delta^{4,9(11)}$- or $\Delta^{5,9(11)}$-double bonds, three double bonds, e.g., $\Delta^{1,4,9(11)}$-, $\Delta^{1,3,5(10)}$-, $\Delta^{2,5(10),9}$- or $\Delta^{3,5,9(11)}$-double bonds, or four double bonds, e.g., $\Delta^{1,3,5(10),9(11)}$-double bonds.

In view of the commercial usefulness of the products of this process, preferred starting compounds for the process of this invention are 20-cyano steroids of general Formula II wherein St is a group of one of partial formulae $St_1$ to $St_6$:

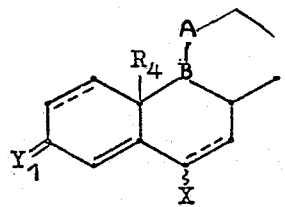

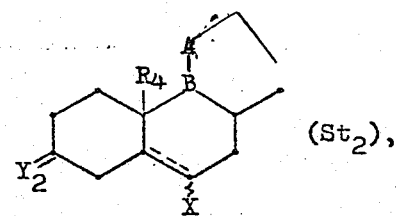

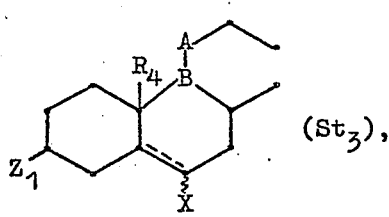

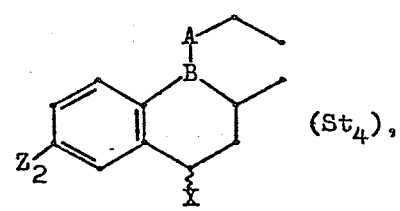

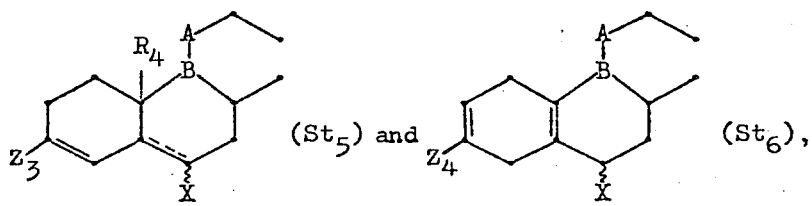

wherein —A—B— is —CH$_2$—CH<, —CHOH—CV<, —CO—CV<, or —CH=C< group, in which V is a hydrogen atom, a fluorine atom, or a chlorine atom; X is a hydrogen atom, methyl, or a fluorine atom; $Y_1$ is a free or ketalized oxo, ketalized ox is preferably being alkylenedioxy of 1–8 carbon atoms forming with the 3-position carbon atom a 5 or 6 membered ring or o-phenylenedioxy; $Y_2$ is a ketalized oxo, preferably as defined for $Y_1$; $Z_1$ and $Z_2$ each is a free, esterified, or etherified hydroxy group, esterified hydroxy perferably being alkanoyloxy of 1–8 carbon atoms or benzoyloxy and etherified hydroxy perferably being alkoxy of 1–8 carbon atoms or benzyloxy; $Z_3$ and $Z_4$ each is an etherified hydroxy group, preferably alkoxy of 1–8 carbon atoms or benzyloxy; $R_4$ is a hydrogen atom or methyl; and $====$ is a single or double bond.

When $Z_1$ and $Z_2$ are ketalized oxo groups, they preferably are o-phenylenedioxy or alkylenedioxy having 2–6 carbon atoms in the alkylene group, e.g., ethylenedioxy, 1,3-propylenedioxy, 2,3-butylenedioxy and 2,2-dimethylpropylenedioxy.

When $Z_1$ and $Z_2$ are esterified hydroxy groups, they preferably are benzoyloxy or straight-chain or branched alkanoyloxy of 1–8 carbon atoms, e.g., formyloxy, acetoxy, propionyloxy, dimethylacetoxy, trimethylacetoxy, butyryloxy, tert.-butylacetoxy, hexanoyloxy and octanoyloxy.

When $Z_1$, $Z_2$, $Z_3$, or $Z_4$ are etherified hydroxy groups, they preferably are benzyloxy or straight-chain or branched alkoxy group of 1–6 carbon atoms, e.g., methoxy, ethoxy, propoxy, isopropoxy, butoxy, isobutoxy, sec.-butoxy and tert.-butoxy.

Suitable starting compounds for the process of this invention, in addition to the free 21-carboxy acids, are those of general Formula II wherein $R_3$ is benzyl or alkyl of 1–8 carbon atoms, e.g., the methyl, ethyl, propyl, isopropyl, butyl, sec.-butyl and tert.-butyl. Others include pentyl, hexyl and octyl. As will be obvious to those skilled in the art, equivalents as starting materials are those wherein $R_3$ is a benzyl group bearing one or more ring substituents, e.g., Cl or $CH_3$, or is an unsaturated alkyl group or one bearing one or more simple substituents, e.g., hydroxy or alkoxy, or is a cycloalkyl group.

The starting materials of Formula II are readily prepared, as noted above, from the corresponding 17-oxo steroids of the general Formula III

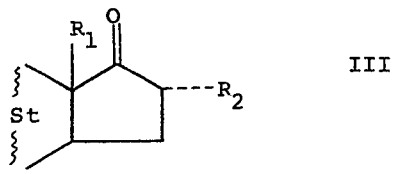

III wherein $R_1$, $R_2$, and St have the above-mentioned meanings.

The process of this invention is conducted in an aprotic solvent, e.g., polar ethers, for example, glycol dimethyl ether, tetrahydrofuran, or dioxane, and dipolar aprotic solvents, e.g., acetonitrile, dimethyl sulfoxide, N-methylpyrrolidone, hexamethylphosphoric triamide, or especially dimethylformamide.

The process of this invention requires a deprotonating agent which contains an alkali metal, an alkaline earth metal, copper(I) or thallium(I). A deprotonating agent is one which removes a hydrogen atom from an activated carbon atom, in this case the $C_{20}$ carbon atom activated by the 20-cyano and 21-carboxy groups, and replaces it by another anion, usually supplied by the deprotonating agent.

Suitable deprotonating agents for the process of this invention include the alkali hydrides and alkaline earth hydrides, e.g., sodium hydride, potassium hydride, calcium hydride, and particularly lithium hydride; the alkali amides, e.g., sodium amide; the alkali alcoholates, alkaline earth alcoholates, copper(I) alcoholates and thallium(I) alcoholates of 1–6 carbon atoms in the alcoholate group, e.g. sodium methylate, potassium tert.-butylate, magnesium ethylate, copper(I) tert.-butylate, and thallium ethylate.

Particularly high yields of the product of the process are obtained if the deprotonating step is conducted by first reacting a compound of Formula II in a aprotic solvent initially with an alkali hydride, preferably lithium hydride, and then treating the reaction mixture with an excess of a water soluble inorganic thallium(I) salt, a silver(I) salt, or especially a copper(I) salt, e.g., copper(I) chloride, copper(I) bromide, copper(I) iodide, copper(I) cyanide, copper(I) rhodanate, copper(I) sulfate, thallium(I) sulfate thallium(I) fluoride, silver(I) nitrate, silver(I) perchlorate, or silver(I) tetrafluoborate. In this reaction, sufficient excess of the copper(I) salts, thallium(I) salts or silver(I) salt is employed so that a portion thereof remains undissolved as a sediment.

The deprotonating step of the compounds of general Formula II is preferably effected at a reaction temperature of from 0° C. to 100° C., more preferably from 30°C to 75° C.

After deprotonating the starting compound, oxygen or air is introduced into the reaction mixture to split the deprotonated compound of general Formula II by oxidation. This is preferably accomplished at a reaction temperature of from 0° C. to 60° C., preferably from 10° C to 40° C.

The optimum reaction time for this oxidative splitting process depends on the selected starting compound, solvent, and the specific reaction temperature and can readily be determined, e.g., employing the usual analytical techniques, for example, thin-layer chromatography, with samples of the reaction mixture taken at successive time intervals.

If a 3-keto-$\Delta^4$-steroid is employed as a starting compound for the process of this invention, these are not only autoxidized in the 20-position, but additionally also at least partially oxidized in the 6-position. To avoid this side reaction, it is advantageous to first block the 3-keto group, e.g., by ketalization, and then split off the blocking group after the oxidative splitting step has been accomplished.

It is surprising that the compounds of general Formula II can be converted by oxidation with gaseous oxygen, under the conditions of the process of this invention, to compounds of general Formula I, particularly since it is known that steroids with a progesterone side chain, i.e., 20-oxo steroids, under comparable conditions, are oxidized in the 17$\alpha$-position, under these conditions with the side chain being split off. J. Org. Chem. 33, 1968, 3294; and Chem and Ind. [London], 1966, 25.

By the process of this invention it is possible to prepare numerous, pharmacologically effective, known compounds. Moreover, it is also possible to produce heretofore unknown 17$\beta$-oxalyl steroids of general Formula I which likewise are pharmacologically active or which can serve as intermediates for the production of pharmacologically effective substances. Thus, for example, 17$\beta$-oxalyl steroids of the general Formula I carrying the residue $St_1$ as the steroid residue, other than those which possess a $\Delta^{9(11)}$-double bond, are pharmacologically active substances which are distinguished, in particular, by a good topical anti-inflammatory effectiveness and the absence of systemic side effects.

Compounds of general Formula I having a steroid residue $St_1$ and a $\Delta^{9(11)}$-double bond are valuable intermediates for the preparation of the corresponding 9$\alpha$-halo-11$\beta$-hydroxy steroids (Belgian Pat. No. 779,869).

Compounds of general Formula I with a steroid residue $St_4$ likewise possess hormonal activity.

Compounds of general Formula I with a steroid residue $St_2$, $St_3$, $St_5$, or $St_6$ are valuable intermediate products which, after ketal splitting, saponification and/or oxidation under conventional conditions, can readily be converted into compounds of general Formula I with a steroid residue $St_1$.

Examples of novel compounds produced according to the process of this invention are:

a. 3-oxy-1,3,5(10)-pregnatriene-21-oic acids of the formula

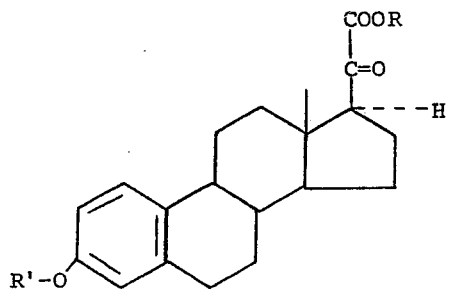

wherein R and R' each are alkyl of 1–8 carbon atoms;

b. 3,20-dioxo-4-pregnen-21-oic acid alkyl esters of the formula

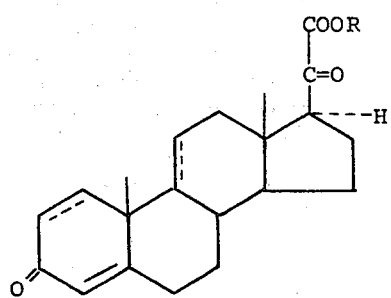

wherein R is alkyl of 1–8 carbon atoms and ==== is a single or double bond; and c. 20-oxo-5-pregnen-4-oic acid alkyl esters of the formula

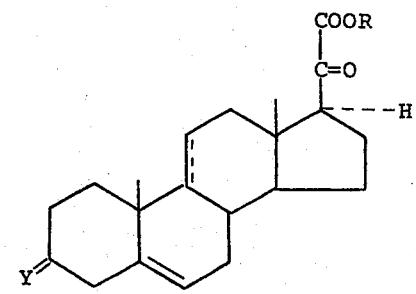

wherein R is alkyl of 1–8 carbon atoms, Y is $\beta$-OH,$\alpha$-H, $\beta$-AcO,$\alpha$-H wherein Ac is alkanoyl of 1–8 carbon atoms or benzoyl, or alkylenedioxy of 2–8 carbon atoms forming with the 3 position carbon atom a 5 or 6 membered ring, and ==== is a single or double bond.

The predominantly novel starting compounds of general Formula II can be obtained in a manner known per se from the corresponding 17-oxo steroids. However, in the synthesis of these starting compounds, it is unnecessary to begin with 17-oxo steroids of general Formula III wherein all finally desired substituents are already present. Rather, it is also possible to introduce the lastly desired substituents after the side chain has been constructed. Thus, for example, 17-oxo steroids of general Formula III having a $\Delta^{9(11)}$-double bond can be converted into the cyano steroids of general Formula II, according to the process of this invention, and the $\Delta^{9(11)}$-double bond of these compounds can thereafter be converted into, e.g., a 9$\alpha$-halo-11$\beta$-hydroxy group, by conventional processes.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsover. In the following examples, all temperatures are set forth uncorrected in degrees Celsius; unless otherwise indicated, all parts and percentages are by weight.

EXAMPLE 1 a. 61 g. of 3-methoxy-1,3,5(10)-estratrien-17-one is combined with 130 ml. of absolute benzene, 86 ml. of glacial acetic acid, 65 ml. of ethyl cyanoacetate, and g. of β-alanine, and refluxed for 28 hours on a water trap filled with a 4 A molecular sieve. The mixture is then concentrated under vacuum, the residue is taken up in methylene chloride, the methylene chloride solution is washed with sodium bicarbonate solution and water, dried over magnesium sulfate, and concentrated under vacuum. The residue is recrystallized from ethanol, thus obtaining 72.5 g. of the ethyl ester of 20-cyano-3-methoxy-19-nor-1,3,5(10),17(20)-pregnatetraene-21-oic acid, m.p. 152°C.

$[\alpha]_D^{20} = +49.5°$ (chloroform; c = 1%).

b. 60.0 g. of the ethyl ester of 20-cyano-3-methoxy-19-nor-1,3,5(10),17(20)-pregnatetraene-21-oic acid is mixed with 300 ml. of tetrahydrofuran and 2 ml. of N/10 sodium hydroxide solution and, after adding 5 g. of 10% palladium-animal charcoal catalyst, hydrogenated with hydrogen for 10 minutes at room temperature under normal pressure. The catalyst is then filtered off, the filtrate concentrated under vacuum, and the residue taken up in ether, filtered over silica gel, and the filtrate concentrated under vacuum. The thus-produced residue is recrystallized from ethanol-ether, thus obtaining 45.6 g. of the ethyl ester of 20-cyano-3-methoxy-19-nor-1,3,5(10)-pregnatriene-21-oic acid, m.p. 118° C.

$[\alpha]_D^{20} = +43.7°$ (chloroform; c = 1%).

c. An oxygen-free solution of 7.6 g. of the ethyl ester of 20-cyano-3-methoxy- 19-nor-1,3,5(10)-pregnatriene-21-oic acid in 100 ml. of freshly distilled, absolute dimethylformamide is combined with 190 mg. of lithium hydride; the mixture is heated to 50° C. for 30 minutes under argon. The mixture is then allowed to cool, combined with 3 g. of cooper (I) iodide, again heated to 50° C., recooled, and then dry oxygen is passed through the solution for one hour at room temperature. Thereafter, the reaction mixture is cooled to about 5° C., mixed with 30 ml. of 10% aqueous acetic acid, as well as 200 ml. of water, and extracted with ether. The ether phase is washed, dried, and concentrated under vacuum. The residue is dried in a high vacuum, and then is recrystallized from ethanol-ether, thus producing 6.2 g. of the ethyl ester of 3-methoxy-20-oxo-19-nor-1,3,5(10)-pregnatriene-21-oic acid, m.p. 109° C.

$[\alpha]_D^{20} = +136°$ (chloroform; c = 1%).

EXAMPLE 2

An oxygen-free solution of 7.6 g. of the ethyl ester of 20-cyano-3-methoxy-19-nor-1,3,5(10)-pregnatriene-21-oic acid in 100 ml. of freshly distilled, absolute dimethylformamide is combined with 190 mg. of lithium hydride, and the mixture is heated for 30 minutes to 50° C. under argon. The reaction mixture is then allowed to cool to room temperature, and dry oxygen is passed for one hour through the solution. The mixture is worked up as described in Example 1(c), and the crude product is chromatographed over a silica gel column, thus obtaining 2.9 g. of the ethyl ester of 3-methoxy-20-oxo-19-nor-1,3,5(10)-pregnatriene-21-oic acid, m.p. 108° C. (from ethanol-ether).

EXAMPLE 3

2.7 g. of potassium tert.-butylate is introduced into an oxygen-free solution of 7.6 g. of the ethyl ester of 20-cyano-3-methoxy-19-nor-1,3,5(10)-pregnatriene-21-oic acid in 100 ml. of freshly distilled, absolute dimethylformamide; the mixture is heated under argon for 30 minutes to 50° C. The reaction mixture is then allowed to cool to room temperature, and oxygen is passed through the solution for 1 hour. The reaction mixture is worked up as described in Example 2, thus obtaining 1.6 g. of the ethyl ester of 3-methoxy-20-oxo-19-nor-1,3,5(10)-pregnatriene-21-oic acid, m.p. 108° C. (from ethanol-ether).

EXAMPLE 4

An oxygen-free solution of 7.6 g. of the ethyl ester of 20-cyano-3-methoxy-19-nor-1,3,5(10)-pregnatriene-21-oic acid in 100 ml. of freshly distilled, absolute dimethylformamide is combined with 3.3 g. of freshly prepared copper (I) tert.-butylate; the mixture is heated for 30 minutes under argon to 50° C. Then, the mixture is allowed to cool, and oxygen is passed for one hour through the solution. The latter is worked up as described in Example 1(c), thus obtaining 6.5 g. of the ethyl ester of 3-methoxy-20-oxo-19-nor-1,3,5(10)-pregnatriene-21-oic acid, m.p. 109° C.

EXAMPLE 5

5.0 g. of freshly prepared thallium(I) ethylate is introduced into an oxygen-free solution of 7.6 g. of the ethyl ester of 20-cyano-3-methoxy-19-nor-1,3,5(10)-pregnatriene-21-oic acid in 100 ml. of freshly distilled, absolute dimethylformamide, and the mixture is heated for 30 minutes to 50° C. The mixture is then allowed to cool to room temperature, and oxygen is passed for one hour through the solution. The reaction mixture is then worked up as described in Example 2, thus obtaining 3.1 g. of the ethyl ester of 3-methoxy-20-oxo-19-nor-1,3,5(10)-pregnatriene-21-oic acid, m.p. 107°–108° C. (from ethanol-ether).

EXAMPLE 6 a. 50 g. of 3β-hydroxy-5-androsten-17-one is combined with 110 ml. of absolute benzene, 70 ml. of glacial acetic acid, 55 ml. of ethyl cyanoacetate, and 8.5 g. of β-alanine, and the mixture is refluxed for 18 hours on a water trap filled with a 4 A molecular sieve. The reaction mixture is then worked up as described in Example 1(a) and, after recrystallization from acetone-hexane, one obtains 41.3 g. of the ethyl ester of 3β-hydroxy-20-cyano-5,17(20)-pregnadiene-21-oic acid, m.p. 152° C.

$[\alpha]_D^{20} = +47°$ (chloroform; c = 1%).

b. 36.9 g. of the ethyl ester of 3β-hydroxy-20-cyano-5,17(20)-pregnadiene-21-oic acid is mixed with 500 ml. of ethanol and 3 g. of 10% palladium-charcoal catalyst and hydrogenated under normal pressure for one hour at room temperature. The reaction mixture is then worked up as set forth in Example 1(b), thus producing 28.3 g. of 3β-hydroxy-20-cyano-5-pregnene-21-oic acid ethyl ester, m.p. 62.5°–100° C.

$[\alpha]_D^{20} = +46.7°$ (chloroform; c = 1%).

c. Under the conditions disclosed in Example 1(c), 11.6 g. of the ethyl ester of 3β-hydroxy-20-cyano-5-pregnene-21-oic acid in 150 ml. of absolute dimethylformamide is reacted with 360 mg. of lithium hydride, 2.5 g. of copper(I) bromide, and oxygen. The reaction mixture is worked up as described in Example 1(c), thus producing 7.95 g. of the ethyl ester of 3β-hydroxy-20-oxo-5-pregnene-21-oic acid, m.p. 84° C. (from diisopropyl ether).

$[\alpha]_D^{20} = +28°$ (chloroform; c = 0.5%).

EXAMPLE 7 a. 37 g. of the ethyl ester of 3β-acetoxy-20-cyano-5,17(20)-pregnadiene-21-oic acid is mixed in 450 ml. of tetrahydrofuran and 150 ml. of ethanol with 2.5 g. of 10% palladium-charcoal catalyst and 2 ml. of N/10 sodium hydroxide solution and hydrogenated under normal pressure with hydrogen at room temperature. The reaction mixture is worked up as set forth in Example 1(b), thus obtaining the ethyl ester of 3β-acetoxy-20-cyano-5-pregnene-21-oic acid (34 g.), m.p. 170° C.

$[\alpha]_D^{20} = -61.4°$ (chloroform; c = 1%).

b. Under the conditions described in Example 1(c), 30 g. of the ethyl ester of 3β-acetoxy-20-cyano-5-pregnene-21-oic acid is split by oxidation, thus producing 22.9 g. of the ethyl ester of 3β-acetoxy-20-oxo-5-pregnene-21-oic acid as a viscous, unstable oil.

c. The ethyl ester of 3β-acetoxy-20-oxo-5-pregnene-21-oic acid produced according to Example 7(b) is mixed in 150 ml. of freshly distilled, absolute ethanol with 6 g. of sodium ethylate and agitated for 4 hours under nitrogen at room temperature. The reaction mixture is then cooled to about 5° C., neutralized by adding 10% aqueous acetic acid, concentrated under vacuum to one-third its original volume, extracted with ether, the ether phase is washed, dried, and concentrated under vacuum. The remainder is recrystallized from diisopropyl ether, thus obtaining 16.9 g. of the ethyl ester of 3β-hydroxy-20-oxo-5-pregnene-21-oic acid, m.p. 84° C.

$[\alpha]_D^{20} = +28°$ (chloroform; c = 0.5%).

d. Under nitrogen, 13.5 ml. of a standard solution of Jones reagent (J. Chem. Soc. [London] 1953, 2548) is added to a solution of 16.5 g. of the ethyl ester of 3β-hydroxy-20-oxo-5-pregnene-21-oic acid in 1,200 ml. of acetone distilled over potassium permanganate, which latter solution is cooled to about 10° C. The excess Jones reagent is then destroyed by adding methanol, the mixture is extensively concentrated under vacuum, and the residue is combined with water and extracted with methylene chloride. The methylene chloride phase is washed, dried over magnesium sulfate, and concentrated under vacuum.

The thus-obtained residue is mixed with 150 ml. of absolute ethanol and 1.5 g. of potassium tert.-butylate and refluxed under argon for 10 minutes. The mixture is then poured into saturated sodium phosphate, dibasic, solution. The mixture is extracted with ether, the ether phase washed and then dried over magnesium sulfate, and concentrated under vacuum. The residue is purified by chromatography over a silica gel column, and the obtained crude product is recrystallized from acetonehexane, thus producing 7.9 g. of the ethyl ester of 3,20-dioxo-4-pregnene-21-oic acid, m.p. 106° C.

$[\alpha]_D^{20} = +197°$ (chloroform; c = 1%).

EXAMPLE 8 a. 33 g. of 17β-acetoxy-4-androsten-3-one is mixed with 52 g. of 2,2-dimethylpropanediol, 25 ml. of triethyl formate, 250 ml. of absolute methylene chloride, and 500 mg. of anhydrous p-toluenesulfonic acid and then refluxed under argon for 6 hours.

The reaction mixture is then allowed to cool, washed with sodium bicarbonate solution and water, dried over sodium sulfate, and concentrated under vacuum. The residue is recrystallized from acetone, thus obtaining 35.8 g. of 17β-acetoxy-3,3-(2',2'-dimethylpropylenedioxy)-5-androstene, m.p. 199° C.

$[\alpha]_D^{20} = -49°$ (chloroform; c = 1%).

b. 35 g. of 17β-acetoxy-3,3-(2',2'-dimethylpropylenedioxy)-5-androstene is combined with 100 ml. of absolute ethanol and 1.5 g. of sodium ethylate and agitated for 12 hours under argon. The reaction mixture is then concentrated under vacuum, the residue is mixed with dilute acetic acid, extracted with ether, the ether phase washed and dried over magnesium sulfate. The ether phase is then concentrated under vacuum, the remainder is recrystallized from methylene chloride-chloroform, and the yield is 32.3 g. of 17β-hydroxy-3,3-(2',2'-dimethylpropylenedioxy)-5-androstene, m.p. 215° C.

$[\alpha]_D^{20} = -3.5°$ (methanol; c = 1%).

c. 35 g. of chromium (VI) oxide, dried over phosphorus pentoxide, is added in incremental portions to a mixture, cooled to about 5° C., of 400 ml. of methylene chloride and 56.5 g. of absolute pyridine; the mixture is then agitated for 15 minutes at room temperature. Then, 29 g. of 17β-hydroxy-3,3-(2',2'-dimethylpropylenedioxy)-5-androstene is added to the mixture and the latter is stirred for 2 hours at room temperature. The mixture is thereafter extensively concentrated under vacuum, mixed with ethyl acetate, filtered, the filtrate washed with 1N potassium hydroxide solution and water, and dried over magnesium sulfate. The solution is concentrated to 100 ml. under vacuum, the thus-separated product is filtered off and recrystallized from acetonemethylene chloride, thus obtaining 24.1 g. of 3,3-(2',2'-dimethylpropylenedioxy)-5-androsten-17-one, m.p. 205° C.

$[\alpha]_D^{20} = +9.8°$ (chloroform; c = 1%).

d. 15 g. of 3,3-(2',2'-dimethylpropylenedioxy)-5-androsten-17-one is combined with 300 ml. of absolute ethanol, 40 ml. of ethyl cyanoacetate, and 30 g. of potassium fluoride and heated for 3 days to 110° C. in a tumbling autoclave. The mixture is filtered, the filtrate is mixed with ethyl acetate, decolorized with activated carbon, and concentrated under vacuum. The residue is purified over a silica gel column; after recrystallization from diisopropyl ether, 10.4 g. of the ethyl ester of 3,3-(2',2'-dimethylpropylenedioxy)-20-cyano-5,17(20)-pregnadiene-21-oic acid is obtained, m.p. 188° C.

$[\alpha]_D^{20} = -15.3°$ (chloroform; c = 1%).

e. 9.5 g. of the ethyl ester of 3,3-(2',2'-dimethylpropylenedioxy)-20-cyano-5,17(20)-pregnadiene-21-oic acid is dissolved in 50 ml. of peroxide-free, absolute tetrahydrofuran. This solution is added dropwise within 15 minutes and under agitation to a suspension, cooled to 5° C., of 210 mg. of sodium borohydride in 15 ml. of peroxide-free, absolute tetrahydrofuran. The mixture is stirred for another 15 minutes, the reaction mixture is poured into 100 ml. of aqueous sodium phosphate, monobasic, solution. The mixture is extracted with methylene chloride, the methylene chloride phase is washed, and then dried over magnesium sulfate and concentrated under vacuum. The residue is recrystallized from acetone-methylene chloride, thus obtaining 8.7 g. of the ethyl ester of 3,3-(2',2'-dimethylpropylenedioxy20-cyano-5-pregnene-21-oic acid, m.p. 168° C.

$[\alpha]_D^{20} = -49.8°$ (chloroform; c = 1%).

f. Under the conditions indicated in Example 1(c), 8.5 g. of the ethyl ester of 3,3-(2',2'-dimethylpropylenedioxy)-20-cyano-5-pregnene-21-oic acid is split by oxidation; for the deprotonating step, 175 mg.

of lithium hydride and 2 g. of copper (I) cyanide are utilized.

The reaction mixture is worked up as described in Example 1(c), thus producing 7.5 g. of the ethyl ester of 3,3-(2',2'-dimethylpropylenedioxy)-20-oxo-5-pregnene-21-oic acid as a crude product.

This crude product is combined, without further purification, with 50 ml. of absolute acetone and 300 mg. of anhydrous p-toluenesulfonic acid, and then allowed to stand for 12 hours at room temperature under an argon atmosphere. Then, a small amount of pyridine is added to the reaction mixture, and the latter is concentrated under vacuum. The residue is chromatographed over a silica gel column and the obtained crude product is recrystallized from acetone/hexane, thus producing 5.20 g. of the ethyl ester of 3,20-dioxo-4-pregnene-21-oic acid, m.p. 105° C.

$[\alpha]_D^{20} = 195°$ (chloroform; c = 1%).

EXAMPLE 9 a. 20 g. of 1,4-androstadiene-3,17-dione is combined with 200 ml. of absolute benzene, 15 ml. of ethyl cyanoacetate, 10 ml. of acetic acid, and 2 g. of β-alanine; the mixture is refluxed for 30 hours on a water trap. Then, the reaction mixture is worked up as set forth in Example 1(a), thus obtaining 17.6 g. of the ethyl ester of 20-cyano-3-oxo-1,4,17(20)-pregnatriene-21-oic acid, m.p. 161–164° C.

$[\alpha]_D^{20} = +159°$ (chloroform; c = 1%).

b. 9.85 g. of the ethyl ester of 20-cyano-3-oxo-1,4,17(20)-pregnatriene-21-oic acid is dissolved in 500 ml. of ethanol, and the solution is cooled to 0° C. Then, 360 mg. of pulverized sodium hydride is added in incremental portions to the solution and the latter agitated for 5 hours at 0° C.

The reaction mixture is worked up as described in Example 8(e), the thus-obtained crude product is recrystallized from acetone-diisopropyl ether, and the yield is 6.72 g. of the ethyl ester of 20-cyano-3-oxo-1,4-pregnadiene-21-oic acid, m.p. 161°–⅞° C.

$[\alpha]_D^{23} = +22.3°$ (chloroform; c = 1%).

c. 3.79 g. of the ethyl ester of 20-cyano-3-oxo-1,4-pregnadiene-21-oic acid is dissolved in 50 ml. of freshly distilled dimethylformamide; argon is passed through the solution, and the latter is heated to 50° C. whereafter it is combined with 96 mg. of lithium hydride and heated for 45 minutes to 50° C. The mixture is then allowed to cool, 1 g. of copper (I) chloride is added thereto, and the mixture is once more heated for 20 minutes to 50° C. The reaction mixture is allowed to cool to room temperature, and dry air is passed through the solution for 3½ hours. After the reaction is terminated, the mixture is poured into 100 ml. of saturated sodium phosphate, dibasic, solution, then extracted with ether, and the ether phase washed and dried over magnesium sulfate, whereupon it is concentrated under vacuum and the residue is recrystallized from diisopropyl ether, thus obtaining 2.83 g. of the ethyl ester of 3,20-dioxo-1,4-pregnadiene-21-oic acid, m.p. 112–114° C.

$[\alpha]_D^{23} = +160°$ (chloroform; c = 1%).

EXAMPLE 10 a. Under the conditions set forth in Example 1(a), 11 g. of 1,4-androstadiene-3,17-dione is reacted with methyl cyanoacetate, thus producing 8.65 g. of the methyl ester of 20-cyano-3-oxo-1,4,17(20)-pregnatriene-21-oic acid, m.p. 197°–203° C. (from diisopropyl ether).

$[\alpha]_D^{23} = +151.5°$ (chloroform; c = 1%).

b. 5.2 g. of the methyl ester of 20-cyano-3-oxo-1,4,17(20)-pregnatriene-21-oic acid is reacted, under the conditions indicated in Example 9(b), in 150 ml. of methanol at 0° C. with 200 mg. of sodium borohydride. After a reaction time of 7 hours, the reaction mixture is worked up as described in Example 9(b), and after recrystallization from methanol, 4.92 g. of the methyl ester of 20-cyano-3-oxo-1,4-pregnadiene-21-oic acid is produced, m.p. 208°–210° C.

$[\alpha]_D^{24} = +24°$ (chloroform; c = 1%).

c. 1.6 g. of the methyl ester of 20-cyano-3-oxo-1,4-pregnadiene-21-oic acid is reacted, under the conditions indicated in Example 9(c), in 23 ml. of absolute dimethylformamide with 50 mg. of lithium hydride, 1 g. of copper(I) chloride, and atmospheric oxygen, and the mixture is then worked up, thus obtaining 798 mg. of the methyl ester of 3,20-dioxo-1,4-pregnadiene-21-oic acid, m.p. 144°–148° C. (from diisopropyl ether).

$[\alpha]_D^{20} = +147°$ (chloroform; c = 1%).

EXAMPLE 11 a. Five grams of 1,4,9(11)-androstatriene-3,17-dione is combined with 50 ml. of benzene, 3,5 ml. of glacial acetic acid, 4.5 ml. of ethyl cyanoacetate, and 1 g. of β-alanine and refluxed for 26 hours on a water trap. The reaction mixture is worked up as described in Example 1(a), the obtained product is purified by chromatography over a silica gel column, and then recrystallized from diisopropyl ether, thus obtaining 3.63 g. of the methyl ester of 20-cyano-3-oxo-1,4,9(11),17(20)-pregnatetraene-21-oic acid, m.p. 192–199° C. $[\alpha]_D^{23} = +133°$ (chloroform; c = 1%).

b. Under the conditions described in Example 9(b), 2 g. of the methyl ester of 20-cyano-3-oxo-1,4,9(11),17(20)-pregnatetraene-21-oic acid in 100 ml. of methanol is reduced within 2 hours with 78 mg. of sodium borohydride and then worked up, yielding 1.43 g. of the methyl ester of 20-cyano-3-oxo-1,4,9(11)-pregnatriene-21-oic acid, m.p. 164–168° C. (from diisopropyl ether). $[\alpha]_D^{23} = -25°$ (chloroform; c = 1%).

c. Under the conditions described in Example 9(c), 1.79 g. of the methyl ester of 20-cyano-3-oxo-1,4,9(11)-pregnatriene-21-oic acid in 25 ml. of absolute dimethylformamide is reacted with 60 mg. of lithium hydride and 500 mg. of copper(I) chloride. Then, dry air is passed through the solution for one hour at room temperature, and the solution is worked up as set forth in Example 9(c), thus obtaining 1.32 g. of the methyl ester of 3,20-dioxo-1,4,9(11)-pregnatriene-21-oic acid, m.p. 194°–196° C. (from diisopropyl ether). $[\alpha]_D^{23} = +94°$ (chloroform; c = 1%).

EXAMPLE 12 a. 6.4 g. of 3,3-ethylenedioxy-5,9(11)-androstadien-17-one is combined with 10 g. of potassium fluoride, 8 ml. of methyl cyanoacetate, and 75 ml. of methanol and refluxed for two days. The reaction mixture is then worked up as described in Example 8(d), yielding 6.9 g. of the methyl ester of 3,3-ethylenedioxy-20-cyano-5,9(11),17(20)-pregnatriene-21-oic acid, m.p. 229° C. (from acetone-hexane). $[\alpha]_D^{20} = +28.2°$ (chloroform; c = 1%).

b. 6.5 g. of the methyl ester of 3,3-ethylenedioxy-20-cyano-5,9(11),17(20)-pregnatriene-21-oic acid is reacted, under the conditions set forth in Example 8(e), in tetrahydrofuran with sodium borohydride, thus obtaining 5.8 g. of the methyl ester of 3,3-ethylenedioxy-20-cyano-5,9(11)-pregnadiene-21-oic acid, m.p. 194° C. $[\alpha]_D^{20} = -23°$ (chloroform; c = 1%).

c. Under the conditions set forth in Example 8(f), 5 g. of the methyl ester of 3,3-ethylenedioxy-20-cyano-5,9(11)-pregnadiene-21-oic acid is split by oxidation, yielding 4 g. of the methyl ester of 3,3-ethylenedioxy-20-oxo-5,9(11)-pregnadiene-21-oic acid as the crude product.

This crude product is combined, without any further purification, with 100 ml. of absolute acetone and 400 mg. of anhydrous p-toluenesulfonic acid and allowed to stand for 5 hours under nitrogen at room temperature. The reaction mixture is then worked up as described in Example 8(f), and after recrystallization from acetone-hexane, 3.1 g. of the methyl ester of 3,20-dioxo-4,9(11)-pregnadiene-21-oic acid is obtained, m.p. 122° C. $[\alpha]_D^{20} = +169°$ (chloroform; c = 1%).

EXAMPLE 13 a. 10 g. of 3,3-(2',2'-dimethylpropylenedioxy)-5-androsten-17-one is combined with 20 g. of potassium fluoride, 25 ml. of butyl cyanoacetate, and 200 ml. of butanol; the mixture is heated for 4 days to 130° C. in a tumbler autoclave.

The reaction mixture is then worked up as described in Example 8(d), thus obtaining 9.2 g. of the butyl ester of 3,3-(2',2'-dimethylpropylenedioxy)-20-cyano-5,17(20)-pregnadiene-21-oic acid, obtained as a vitrifying mass. $[\alpha]_D^{20} = -14°$ (chloroform; c = 1%).

b. Under the conditions disclosed in Example 8(e), 9 g. of 3,3-(2',2'-dimethylpropylenedioxy)-20-cyano-5,17(20)-pregnadiene-21-oic acid butyl ester in tetrahydrofuran is reduced with sodium borohydride, thus obtaining 7.95 g. of the butyl ester of 3,3-(2',2'-dimethylpropylenedioxy)-20-cyano-5-pregnene-21-oic acid as a viscous oil. $[\alpha]_D^{20} = -45°$ (chloroform; c = 1%).

c. Under the conditions set forth in Example 8(f), 7.5 g. of the butyl ester of 3,3-(2',2'-dimethylpropylenedioxy)-20-cyano-5-pregnene-21-oic acid is split by oxidation, yielding 5.8 g. of the butyl ester of 3,3-(2',2'-dimethylpropylenedioxy)-20-oxo-5-pregnene-21-oic acid as the crude product. The thus-obtained crude product is combined with 50 ml. of absolute acetone and 350 mg. of anhydrous p-toluenesulfonic acid and stored for 5 hours under an argon atmosphere at room temperature. The reaction mixture is worked up as set forth in Example 8(f), and the thus-obtained product is purified by chromatography over a silica gel column, yielding 4.1 g. of the butyl ester of 3,20-dioxo-4-pregnene-21-oic acid in the form of a colorless oil. $[\alpha]_D^{20} = -188°$ (chloroform; c = 1%).

EXAMPLE 14

An oxygen-free solution of 2.5 g. of 20-cyano-3-methoxy-19-nor-1,3,5(10)-pregnatriene-21-oic acid ethyl ester in 40 ml. of absolute dimethylformamide is combined with 65 mg. of lithium hydride, and the mixture is heated for 30 minutes to 50° C. under argon. The mixture is then allowed to cool, mixed with 1.5 g. of silver perchlorate, and the mixture is allowed to stand at room temperature for 16 hours under argon. Thereafter, oxygen is passed for one hour through the solution.

The reaction mixture is worked up as described in Example 1(c), thus obtaining 1.35 g. of the ethyl ester of 3-methoxy-20-oxo-19-nor-1,3,5(10)-pregnatriene-21-oic acid, m.p. 108° C. (from ethanol-ether).

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the production of a 17β-oxalyl-17α-H steroid having as its 17-position substituent an oxalyl group of the formula —CO—COOR wherein R is H, alkyl of 1–8 carbon atoms or benzyl, having a 13-methyl or 13-ethyl group and whose 16-position is unsubstituted or substituted by α-CH₃, which comprises the steps of deprotonating in an aprotic solvent a corresponding 20-cyano-17α-H compound of the formula

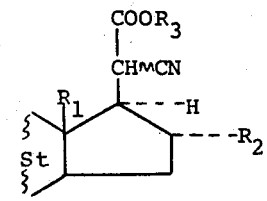

wherein $R_1$ is a methyl or ethyl, $R_2$ is a hydrogen atom or methyl, $R_3$ is a hydrogen atom, alkyl of 1–8 carbon atoms or benzyl, and St is the remainder of the steroid molecule, by reaction with an alkali metal, alkaline earth metal, copper(I) or thallium(I) deprotonating agent, and oxidatively slitting the deprotonated compound with oxygen.

2. A process according to claim 1 wherein St is one of the formulae

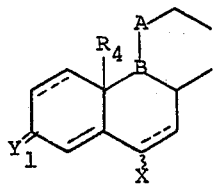 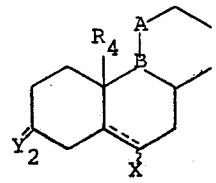

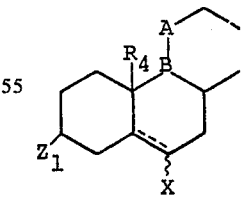 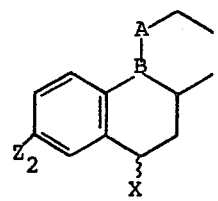

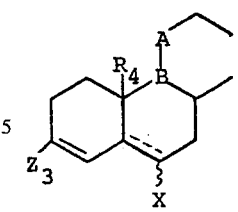 and 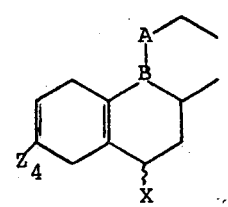

wherein —A—B— is —CH$_2$—CH<, —CHOH—CV<, —CO—CV<, or -CH=C< wherein V is a hydrogen atom, a fluorine atom or a chlorine atom, X is a hydrogen atom, methyl, or a fluorine atom, Y$_1$ is a free or ketalized oxo oxygen atom, Y$_2$ is a ketalized oxo oxygen atom, Z$_1$ and Z$_2$ is a free, esterified, or etherified hydroxy group, Z$_3$ and Z$_4$ each is an etherified hydroxy group, R$_4$ is a hydrogen atom or methyl, and ==== is a single or double bond.

3. A process of claim 2 wherein Y$_1$ is O, o-phenylenedioxy or alkylenedioxy of 1–8 carbon atoms forming with the 3-position carbon atom a 5 or 6 membered ring, Y$_2$ is Y$_1$, Z$_1$ and Z$_2$ are HO, alkoxy of 1–8 carbon atoms, benzyloxy or alkanoyloxy of 1–8 carbon atoms and Z$_3$ and Z$_4$ each is alkoxy of 1–8 carbon atoms or benzyloxy.

4. A process according to claim 1 wherein the starting 20-cyano steroid is first reacted with an alkali hydride and thereafter with a water soluble inorganic copper(I), thallium(I) or silver(I) salt.

5. A process according to claim 4 wherein the salt is a copper(I) salt.

6. A process according to claim 5 wherein the aprotic solvent is dimethylformamide.

7. A 3-oxy-1,3,5(10)-pregnatriene-21-oic acid of the formula

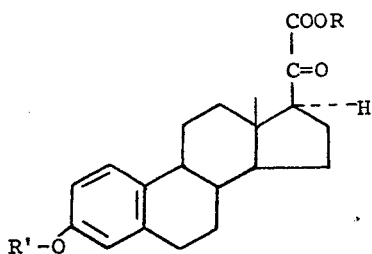

wherein R and R' each are alkyl of 1–8 carbon atoms.

8. A 3,20-dioxo-4-pregnen-21-oic acid alkyl ester of the formula

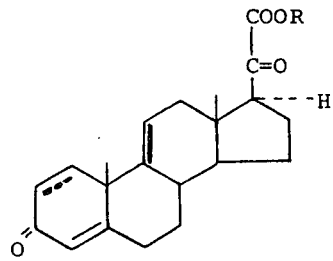

wherein R is alkyl of 1–8 carbon atoms and ==== is a single or double bond.

9. A 20-oxo-5-pregnen-21-oic acid alkyl ester of the formula

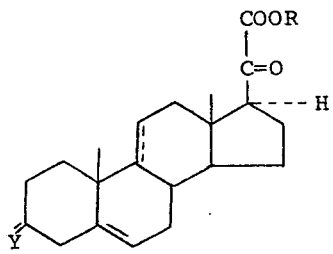

wherein R is alkyl of 1–8 carbon atoms, Y is β-OH,α-H, β-AcO,α-H wherein Ac is alkanoyl of 1–8 carbon atoms or benzoyl, or alkylenedioxy of 2–8 carbon atoms forming with the 3-position carbon atom a 5 or 6 membered ring, and ==== is a single or double bond.

10. A Compound of claim 7, ethyl ester of 3-methoxy-20-oxo-19-nor-1,3,5(10)-pregnatriene-21-oic acid.

11. A compound of claim 9, ethyl ester of 3β-hydroxy-20-oxo-5-pregnene-21-oic acid.

12. A compound of claim 9, ethyl ester of 3β-acetoxy-20-oxo-5-pregnene-21-oic acid.

13. A compound of claim 9, ethyl ester of 3,3-(2',2'-dimethylpropylenedioxy)-20-oxo-5-pregnene-21-oic acid.

14. A compound of claim 8, methyl ester of 3,20-dioxo-1,4,9(11)-pregnatriene-21-oic acid.

15. A compound of claim 9, methyl ester of 3,3-ethylenedioxy-20-oxo-5,9(11)-pregnadiene-21-oic acid.

16. A compound of claim 8, methyl ester of 3,20-dioxo-4,9(11)-pregnadiene-21-oic acid.

17. A compound of claim 9, butyl ester of 3,3-(2',2'-dimethylpropylenedioxy)-20-oxo-5-pregnene-21-oic acid.

* * * * *